United States Patent [19]

Grabinger et al.

[11] 4,021,424
[45] May 3, 1977

[54] S-TRIAZINES

[75] Inventors: Hans Grabinger; Richard Sehring, both of Ingelheim am Rhein, Germany

[73] Assignee: Celamerck GmbH & Co. KG, Ingelheim am Rhein, Germany

[22] Filed: May 19, 1975

[21] Appl. No.: 579,015

[30] Foreign Application Priority Data

May 24, 1974 Germany .......................... 2425287

[52] U.S. Cl. ................ 260/249.8; 71/93; 260/249.5
[51] Int. Cl.² ............. C07D 251/50; C07D 251/52
[58] Field of Search ................. 260/249.8

[56] References Cited
UNITED STATES PATENTS 3,732,220  5/1973  O'Brien et al. ............... 260/249.8

Primary Examiner—John M. Ford
Attorney, Agent, or Firm—Hammond & Littell

[57] ABSTRACT

Novel s-triazines of the formula

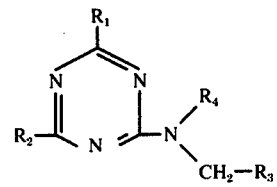

wherein $R_1$ is selected from the group consisting of chlorine and methylthio, $R_2$ is selected from the group consisting of mono- and dialkylamino with alkyls of 1 to 4 carbon atoms, $R_3$ is selected from the group consisting of chlorine, methylthio, ethylthio and mono- and dialkylamino with alkyls of 1 to 4 carbon atoms and $R_4$ is alkyl of 1 to 4 carbon atoms having herbicidal activity.

7 Claims, No Drawings

S-TRIAZINES

OBJECTS OF THE INVENTION

It is an object of the invention to provide the novel triazine derivatives of formula I and to a novel process for their preparation.

It is a further object of the invention to provide novel herbicidal compositions and to a method of killing weeds.

These and other objects and advantages of the invention will become obvious from the following detailed description.

THE INVENTION

The novel s-triazine derivatives of the invention have the formula

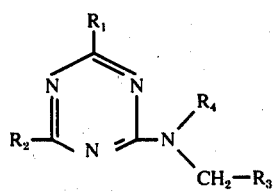

wherein $R_1$ is selected from the group consisting of chlorine and methylthio, $R_2$ is selected from the group consisting of mono- and dialkylamino with alkyls of 1 to 4 carbon atoms, $R_3$ is selected from the group consisting of chlorine, methylthio, ethylthio and mono- and dialkylamino with alkyls of 1 to 4 carbon atoms and $R_4$ is alkyl of 1 to 4 carbon atoms. The alkyls may be straight chained or branched.

The novel products of formula I may be prepared by four reactions illustrated as follows wherein $R_3'$ is selected from the group consisting of methylthio, ethylthio and mono and dialkylamino of 1 to 4 alkyl carbon atoms:

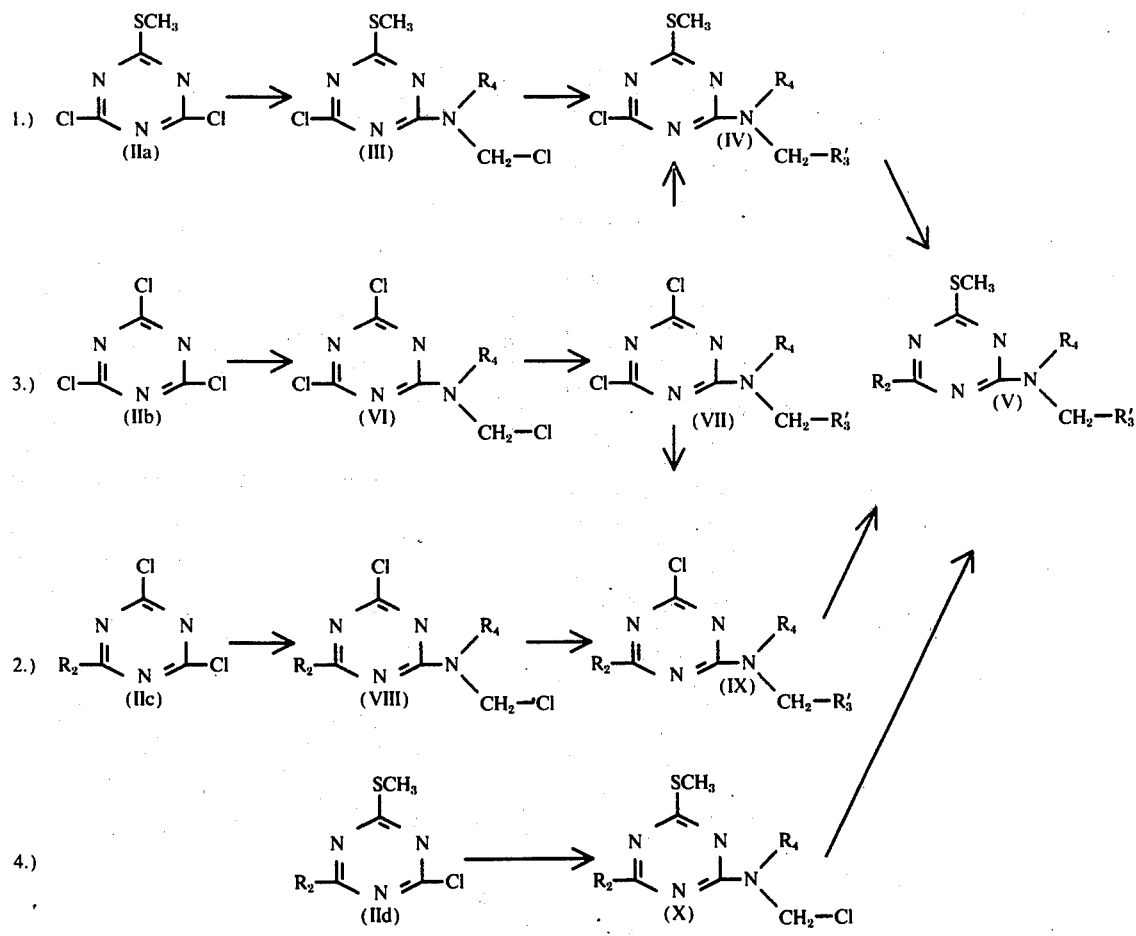

The four processes illustrated above are all based on the unexpected fact that a compound of the formula

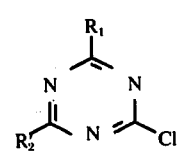

wherein $R_1$ has the above definition and $R_2'$ is selected from the group consisting of chlorine and mono and dialkylamino with alkyl of 1 to 4 carbon atoms will react with a 1,3,5-trialkyl-hexahydrotriazine of the formula

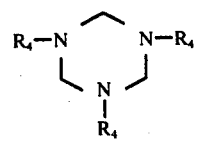

wherein $R_4$ is alkyl of 1 to 4 alkyl carbon atoms according to the reaction scheme

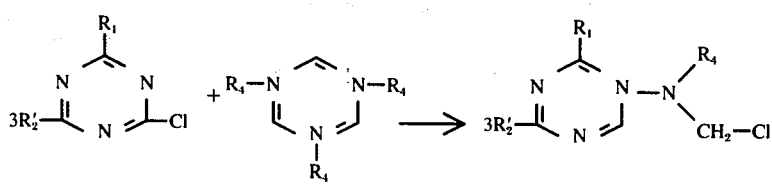

The reaction is effected in at least one inert organic solvent in the absence of water and suitable solvents are chlorinated aliphatic hydrocarbons such as chloroform, methylene chloride, ethylene chloride and carbon tetrachloride. The reaction may be effected at a temperature from 0° C to the reflux temperatures, preferably 20° to 40° C.

The novel herbicidal compositions of the invention are comprised of an effective amount of at least one compound of formula I and a carrier. The amount of the active ingredient may vary from 0.01% to 90% by weight, preferably 0.01 to 10% by weight, of the total composition. The compositions may be in the form of wettable powders, emulsion concentrates, granulates, dusting powders, ultra-low-volume formulations, etc.

The novel method of the invention of killing weeds comprises contacting the weeds with a herbicidally effective amount of at least one compound of formula I. The compounds may be applied either pre-or post-emergence at a rate of 0.5 to 3.0 kg/ha. Examples of susceptible weeds are broad-leaf weeds such as sinapis alba, sinapis arvensis, chenopodium album and amaranthus retroflexus and monocotyledons such as alopecurus myosoroites. The compatibility in maize, peas, carrots, cotton, and rice is above 4 kg/ha.

In the following examples there are described several preferred embodiments to illustrate the invention. However, it should be understood that the invention is not intended to be limited to te specific embodiments.

EXAMPLE 1

2-methylthio-4-(N-isobutyl-N-diethylaminomethyl)-amino-6-isopropylamino-s-triazine A solution of 236 g (1.2 moles) of the dichloride of methylthio cyanuric acid in 2000 ml of chloroform was added at 20° to 25° C over 30 minutes to a solution of 102 g (0.4 moles) of 1,3,5 triisobutyl-hexahydrotriazine in 200 ml of chloroform and the mixture was stirred for one hour with the temperatures rising to 30° C. The mixture was heated at 50° C for one and half hours and was cooled to room temperature. 175.2 g (2.4 moles) of diethylamine were added dropwise to the mixture in an ice bath to keep the temperature below 25° C and the mixture was then stirred for 2 hours at 20° to 25° C.

For identification, the chloroform solution was washed with water to remove amine salts and was evaporated to dryness under reduced pressure to obtain 280 g (80% yield) of 2-methylthio-4-(N-isobutyl-N-diethylaminomethyl)-amino-6-chloro-s-triazine in the form of an oil.

142 g of isopropylamine were added to the chloroform solution of the intermediate at 25° C over 30 minutes and after standing for 10 hours, the mixture was washed 3 times with 300 ml of water, was dried over magnesium sulfate, filtered and evaporated to dryness under reduced pressure to obtain 314 g (76.8% yield) of 2-methylthio-4-(N-isobutyl-N-diethylaminomethyl)-amino-6-isopropylamino-3-triazine as an oil. The oil later solidified as a solid melting at 96° to 98° C.

EXAMPLE 2

2-methylthio-4-(N-isobutyl-N-diethylaminomethyl)-amino-6-isopropylamino-s-triazine A solution of 128 g (0.5 mole) of 1,3,5-triisobutyl-hexahydrotriazine in 200 ml of chloroform was added dropwise at 10° to 15° C over one hour to a solution of 276 g (1.5 moles) of cyanuric acid chloride in 2000 ml of chloroform and after stirring at 40° C for 30 minutes, the mixture was cooled to 15° C. 219 g (3.0 moles) of diethylamine were added dropwise over 45 minutes to the mixture while keeping the temperature below 20° C. Then, 177 g (3.0 moles) of isopropylamine were added dropwise at 20° to 25° C and the mixture was allowed to stand for 2 hours at room temperature. The reaction mixture was washed several times with water, dried and distilled to dryness under reduced pressure to obtain 392 g (79.5% yield) of crude product. 16.5 g (0.05 mole) of the crude product were dissolved in 200 ml of methanol and a solution of 3 g of methylmercaptan and 9 g of 30% sodium methylate in 50 ml of methanol was added dropwise at 20° C to the reaction mixture. The mixture was refluxed for 3 hours and poured into water to obtain an oil of 2-methylthio-4-(N-isobutyl-N-diethylaminomethyl)-amino-6-isopropylamino-s-triazine which was identical to the product of Example 1.

EXAMPLE 3

A solution of 31 g of 2-isopropylamino-4,6-dichloro-s-triazine in 150 ml of chloroform were added dropwise at 5 to 10° C to a solution of 12.8 g (0.05 mole) of 1,3,5-triisobutyl-hexahydrotriazine and the mixture was stirred for 2 hours at 20° C. A solution of 22 g of diethylamine in 100 ml of chloroform was added thereto and the mixture was stirred for 1 hour at 20° C. The mixture was washed with water to remove the hydrochloride salt and dried and distilled to dryness under reduced pressure to obtain a residue of crude 2-isopropylamine-4-(N-isobutyl-N-diethylaminomethyl)-amino-6-chloro-s-triazine. A solution of 3 g of methylmercaptan and 9 g of 30% sodium methylate in 30 ml of methanol was added dropwise at 20° to 25° C to a solution of 16.5 g of the crude product in 150 ml of acetone and the reaction mixture was stirred at 20° C for 2 hours. The mixture was evaporated under reduced pressure to obtain an oil product identical to that of Example 1.

EXAMPLE 4

A solution of 12.8 g (0.05 mole) of 1,3,5-triisobutyl-hexahydrotriazine and 33 g (0.15 mole) of 2-methylthio-4-isopropylamino-6-chloro-s-triazine in 300 ml of chloroform was refluxed for 3 hours while stirring and after cooling to 20° C, 24 g (0.33 mole) of diethylamine were added thereto at 20° – 26° C. The reaction mixture was then treated as in Example 1 to obtain 2-methylthio-4-(N-isobutyl-N-diethylaminomethyl)-amino-6-isopropylamino-s-triazine in the form of an oil identical to the product of Example 1.

EXAMPLE 5

Using the procedure of Example 1, 2-methylthio-4-(N-isobutyl-N-ethylthiomethyl)-amino-6-isopropylamino-s-triazine in the form of an oil with a refractive index $n_D^{20} = 1.5702$ was prepared.

EXAMPLE 6

Using the procedure of Example 1, 2-chloro-4-(N-isobutyl-N-diethylaminomethyl)-amino-6-isopropylamino-s-triazine with a melting point of 109°–111° C was obtained.

EXAMPLE 7

Using the procedure of Example 1, 2-methylthio-4-(N-isobutyl-N-isopropylaminomethyl)-amino-6-isoproylamino-s-triazine in the form of an oil with a refractive index $n_D^{20} = 1.5633$ was obtained.

EXAMPLE 8

Using the procedure of Example 1, 2-chloro-4-(N-isopropyl-N-methylthiomethyl)-amino-6-isopropylamino-s-triazine with a melting point of 138° C was obtained.

EXAMPLE 9

Using the procedure of Example 1, 2-chloro-4-(N-isopropyl-N-isopropylaminomethyl)-amino-6-methylamino-s-triazine in the form of an oil was obtained.

FORMULATION A

A suspension powder was prepared consisting of 25% by weight of the product of Example 1, 55% by weight of Kaolin, 10% by weight of colloidal silicic acid, 9% by weight of lignin sulfonate as a dispersing agent and 1% by weight of sodium tetrapropylene-benzene sulfonate as wetting agent.

FORMULATION B

A suspension powder was prepared comprising of 80% by weight of the compound of Example 1, 8% by weight of calcium lignin sulfonate, 5% by weight of colloidal silicic acid, 5% by weight of sodium sulfate and 2% by weight of sodium diisobutylnaphthalene sulfonate.

FORMULATION C

An emulsion concentrate was prepared comprising 40% by weight of the product of Example 1, 25% by weight of Shellsol A (liquid mixture of aromatic hydrocarbons), 25% by weight of N-methylpyrrolidone and 10% by weight of Emulsogen I 40 (anionic emulsifier) which was diluted with water to a concentration of 0.01 to 10% by weight of the active ingredient for use.

Various modifications of the compositions and methods of the invention may be made without departing from the spirit or scope thereof and it is to be understood that the invention is intended to be limited only as defined in the appended claims.

We claim:
1. A compound selected from the group consisting of 2-methylthio-4-(N-isobutyl-N-diethylaminomethyl-amino)-6-isopropylamino-s-triazine,
2-methylthio-4-(N-isobutyl-N-ethylthiomethyl-amino)-6-isopropylamino-s-triazine,
2-chloro-4-(N-isobutyl-N-diethylaminomethyl-amino)-6-isopropylamino-s-triazine,
2-methylthio-4-(N-isobutyl-N-isopropylaminomethyl-amino)-6-isopropylamino-s-triazine,
2-chloro-4-(N-isopropyl-N-methylthiomethyl-amino)-6-isopropylamino-s-triazine, and
2-chloro-4-(N-isopropyl-N-isopropylaminomethyl-amino)-6-methylamino-s-triazine.
2. The compound of claim 1 which is 2-methylthio-4-(N-isobutyl-N-diethylaminomethyl-amino)-6-isopropylamino-s-triazine.
3. The compound of claim 1 which is 2-methylthio-4-(N-isobutyl-N-ethylthiomethyl-amino)-6-isopropylamino-s-triazine.
4. The compound of claim 1 which is 2-chloro-4-(N-isobutyl-N-diethylaminomethyl-amino)-6-isopropylamino-s-triazine.
5. The compound of claim 1 which is 2-methylthio-4-(N-isobutyl-N-isopropylaminomethyl-amino)-6-isopropylamino-s-triazine.
6. The compound of claim 1 which is 2-chloro-4-(N-isopropyl-N-methylthiomethyl-amino)-isopropylamino-s-triazine.
7. The compound of claim 1 which is 2-chloro-4-(N-isopropyl-N-isopropylaminomethyl-amino)-6-methylamino-s-triazine.

* * * * *